US012773383B2

(12) United States Patent
Yang et al.

(10) Patent No.: US 12,773,383 B2
(45) Date of Patent: Oct. 27, 2026

(54) ETHYLCELLULOSE FORMULATIONS AND METHODS OF MAKING SAME

(71) Applicant: International N&H USA, Inc., Wilmington, DE (US)

(72) Inventors: Hui S. Yang, Plainsboro, NJ (US); Hua Ma, Skillman, NJ (US)

(73) Assignee: International N&H USA, Inc., Wilmington, DE (US)

( * ) Notice: Subject to any disclaimer, the term of this patent is extended or adjusted under 35 U.S.C. 154(b) by 0 days.

(21) Appl. No.: 18/216,818

(22) Filed: Jun. 30, 2023

(65) Prior Publication Data

US 2023/0338268 A1 Oct. 26, 2023

Related U.S. Application Data

(63) Continuation of application No. 16/054,175, filed on Aug. 3, 2018, now abandoned.

(60) Provisional application No. 62/540,900, filed on Aug. 3, 2017.

(51) Int. Cl.

| | |
|---|---|
| ***A61K 8/73*** | (2006.01) |
| ***A61K 8/06*** | (2006.01) |
| ***A61K 8/44*** | (2006.01) |
| ***A61K 8/46*** | (2006.01) |
| ***A61Q 1/02*** | (2006.01) |
| ***A61Q 1/04*** | (2006.01) |
| ***A61Q 17/04*** | (2006.01) |
| ***A61Q 19/00*** | (2006.01) |

(52) U.S. Cl.

CPC ................ *A61K 8/731* (2013.01); *A61K 8/06* (2013.01); *A61K 8/44* (2013.01); *A61K 8/442* (2013.01); *A61K 8/463* (2013.01); *A61Q 1/02* (2013.01); *A61Q 1/04* (2013.01); *A61Q 17/04* (2013.01); *A61Q 19/00* (2013.01); *A61Q 19/007* (2013.01); *A61K 2800/412* (2013.01)

(58) Field of Classification Search

None

See application file for complete search history.

(56) References Cited

U.S. PATENT DOCUMENTS

| | | | | |
|---|---|---|---|---|
| 4,177,177 | A | 12/1979 | Vanderhoff et al. | |
| 4,252,697 | A | 2/1981 | Hashizume et al. | |
| 4,330,338 | A * | 5/1982 | Banker | A23P 20/105 106/170.34 |
| 4,699,799 | A | 10/1987 | Palinczar | |
| 2010/0316684 | A1 | 12/2010 | Daniels | |
| 2013/0280197 | A1* | 10/2013 | Geffroy | A61K 8/345 514/781 |
| 2013/0280198 | A1 | 10/2013 | Cavazutti et al. | |
| 2014/0377202 | A1 | 12/2014 | Lahousse et al. | |
| 2015/0004111 | A1 | 1/2015 | Lahousse | |
| 2016/0106655 | A1 | 4/2016 | Yamada et al. | |

FOREIGN PATENT DOCUMENTS

| | | | | |
|---|---|---|---|---|
| DE | 3710292 | A1 | 10/1988 | |
| FR | 2968973 | B1 | 12/2012 | |
| FR | 2985176 | B1 | 5/2015 | |
| JP | 2014136704 | A | 7/2014 | |
| JP | 2015/199699 | A | 11/2015 | |
| JP | 2017154990 | A | 9/2017 | |
| WO | WO 2013/102566 | A1 | 7/2013 | |
| WO | WO 2013/102570 | A2 | 7/2013 | |
| WO | WO-2015179599 | A1 * | 11/2015 | A61K 8/361 |
| WO | WO-2017053959 | A1 * | 3/2017 | A61K 8/0241 |

OTHER PUBLICATIONS

Day Cream SPF30, Mintel (Jun. 30, 2017), Database GNPD, Database accession No. 4873355 (Year: 2017).*
International Search Report for Itnernational Appln. No. PCT/US2018/045200, mailed Oct. 15, 2018.
Written Opinion of the International Searching Authority, mailed Oct. 15, 2018, in International Appln. No. PCT/US2018/045200.
Anonymous, "Rapid Depigmentation Serum," Mintel, 6 pp. (Jul. 4, 2012), Database GNPD, database accession No. 1810571.
Anonymous, "Refining Cleanse Gentle Peeling, " Mintel, _ pp. (Aug. 26, 2014), Database GNPD, Database accession No. 2620863.
Anonymous, "Day Cream SPF 30," Mintel, _ pp. (Jun. 30, 2017), Database GNPD, Database accession No. 4873355.

* cited by examiner

*Primary Examiner* — H. Sarah Park

(74) *Attorney, Agent, or Firm* — Arnold & Porter Kaye Scholer LLP

(57) ABSTRACT

Ethylcellulose dispersions in water are film forming compositions that have found use in personal care applications. Conventional methods can require that aqueous dispersions of water-insoluble polymers such as ethylcellulose be obtained using surfactants such as sodium lauryl sulfate (SLS). There is a desire to reduce the degree of consumer exposure to SLS in personal care products. The present invention describes ethylcellulose dispersions comprising surfactants to substantially replace sodium lauryl sulfate. The present invention also describes methods of reducing or substantially eliminating SLS in personal care products that comprise ethylcellulose dispersions.

13 Claims, No Drawings

ETHYLCELLULOSE FORMULATIONS AND METHODS OF MAKING SAME

CROSS-REFERENCE TO RELATED APPLICATION

This application is a Continuation of U.S. patent application Ser. No. 16/054,175 filed Aug. 3, 2018, which claims priority of U.S. Patent Application 62/540,900 filed on Aug. 3, 2017, the contents of both applications are incorporated herein by reference in their entirety for all purposes.

FIELD OF THE INVENTION

The present invention relates to compositions suitable for use in personal care products. More particularly, the present invention relates to aqueous polymeric dispersions suitable for use in personal care products having no sodium lauryl sulfate as surfactant, and to methods of producing such compositions.

BACKGROUND OF THE INVENTION

Sodium lauryl sulfate (SLS) is a surfactant that has found widespread use in personal care products, including cosmetic personal care products. While SLS is useful in these applications, its use can have drawbacks. It has been suggested that excessive exposure to SLS can potentially cause skin and ocular damage, and damage to gums and/or hair follicles if misused. Therefore, limiting the exposure of a consumer to SLS, particularly in personal care products intended to be applied to or contacted with skin, can be desirable.

Conventional cosmetic products can include a wide range of concentrations of SLS, depending on the specific product, manufacturer and intended use of the product. According to the Department of Health & Human Services (HHS), SLS can be found in approximately 560 commercial products, with 24 in home cleaning products and 469 in personal care. SLS can be found in these products ranging in concentration from 0.01% to 50% by weight. The Cosmetic Ingredient Review panel of HHS found that, even though SLS is considered safe, the concentration of SLS should not exceed 1% by weight in applications where prolonged contact of SLS with skin is likely. However, the panel noted that the concentration of SLS can be higher than 1% in applications where the duration of skin contact is expected to be brief, discontinuous and/or the product is removed by thorough rinsing after use.

Dispersions of water-insoluble polymers, and in particular alkyl cellulose polymers, are found in a variety of personal care applications, including for example lipsticks, lip balm and other products applied to the lips. SLS is typically used as a surfactant to obtain stable dispersions of alkyl cellulose polymers. However, the use of sodium lauryl sulfate can limit the uses of such dispersions, particularly in cosmetic formulations, due to its anionic nature which limits its use in low pH systems. Sodium lauryl sulfate can also have a destabilizing effect in some cosmetic formulations, which can further limit the use of alkylcellulose dispersions in such formulations.

The use of surfactants in cosmetic formulations containing alkyl cellulose dispersions is complicated and must be balanced with the other elements of the formulation to be effective in achieving the desired properties of the cosmetic. Surfactants for example are often added to improve cleaning, emulsification, solubilizing, conditioning and other effects in a cosmetic formulation.

Because surfactants are surface active agents they are effective in capturing oily particles and are useful for the removal of skin oils when present in cosmetic formulations. Anionic surfactants are those that have a negative charge on their polar head group. They include groups like carboxylic acids, sulfates, sulfonic acids, and phosphoric acid derivatives, and are particularly useful in cleaning applications. Another class of anionic surfactants are the sulfates. Sulfates include synthetic detergents such as sodium lauryl sulfate (SLS), ammonium lauryl sulfate (ALS), or their ethoxylated companions, sodium laureth sulfate (SLES). They are excellent foamers, cleansing agents, and are relatively inexpensive. However, as noted above, they are often irritating to skin and other membranes and alternatives are needed.

In some instances the cosmetic formulation may be designed to add oils back to hair or skin where the oils have been depleted. In the correct concentrations surfactants may form a part of a water, oil and surfactant emulsifier to trap oils and leave them suspended throughout the mixture.

In instances where it is desirable for the cosmetic formulation to be clear, the solubilizing properties of surfactants may be employed. Certain surfactants have the ability to create very small particles where light is able to pass through, giving a clear appearance. These are often use to blend fragrances or other natural ingredients. One example of solubilizing surfactants is polysorbate 20.

Surfactants may also be used to impart various conditioning or aesthetic properties to the cosmetic formulation, creating for example a silky or pearly look and feel and improving stability of the formulation. Surfactants most commonly used for conditioning effects are the cationic surfactants. Cationic surfactants are those that have a positive charge on their polar head group. These surfactants include chemical classes such as Amines, Alkylimidazolines, Alkoxylated Amines, and Quaternized Ammonium Compounds (or Quats). Quats are heavily used as conditioning agents and are nitrogen-containing compounds that acquire a positive charge when dispersed in solution. This positive charge makes them electrostatically attractive to the negative (damaged) sites on hair and skin protein which makes them resist rinse-off. Quats like Cetrimonium chloride and Stearalkonium Chloride provide the basis for numerous hair conditioners. One of the challenges in the art of cosmetic formulation is that cationic and anionic surfactants typically do not work well together and, like the sulfates, can cause irritation.

One solution to the issue of irritation can be the use of amphoteric surfactants. These surfactants have the potential to have both positive and negative charges depending on the environment they are placed. Amphoterics are often used in a secondary capacity, boosting foaming, and improving conditioning and even reduce irritation. However, amphoterics tend to be less effective in cleaning and emulsifying applications and therefore cannot be used as one to one replacement for other surfactants.

Finally, nonionic surfactants are used in all classes of cosmetic formulations for various effects. Non-ionic surfactants are those that contain no specific charge. These are used most often as emulsifiers, conditioning ingredients, and solubilizing agents. The primary nonionics used for cosmetics include alcohols, alkanolamides, esters, and amine oxides.

The object of the present invention is to advance the art by providing methods and cosmetic formulations comprising alkylcellulose dispersions that reduce the level of irritating surfactants, typically the anionic sulfates and most particularly SLS. It will be appreciated from the discussion above that making such a replacement requires careful consideration of how the other elements of the formulation will interact. Additionally, replacement of SLS with another surfactant or combination of surfactants is no guarantee that the cleansing, emulsifying, conditioning or other properties conveyed by the presence of SLS or related sulfates will be maintained. Neither is there any guarantee that the chemical and physical interactions that provide for a stable ethyl cellulose dispersion will not be disrupted and result in less stable, non-homogeneous emulsions, or have deleterious effects on other important properties such as adherence, makeup precision, film uniformity or coating uniformity after application of the dispersion, as well as durability, wearability, and/or persistence of the film dispersion.

The problem to be solved therefore is to provide a composition or formulation suitable for use in most personal care products, where the formulation is substantially free of SLS and yet the formulation retains the physical, chemical and aesthetic properties to which consumers have become accustomed.

SUMMARY OF THE INVENTION

Applicants have solved the stated problem by providing a composition or formulation that is substantially free of SLS and comprising an aqueous dispersion of a water-soluble polymer, typically an alkyl-cellulose, and additionally comprising an alternate surfactant blended into the formulation such that the underlying physical, chemical and aesthetic properties of the formulation are improved or essentially the same as a comparable formulation comprising SLS.

Accordingly the invention provides an aqueous dispersion composition comprising:

a) an alkylcellulose polymer;
b) a surfactant;
c) a stabilizer comprising a non-volatile alcohol having 12 carbons or more;
   wherein the surfactant comprises from about 0.1% to about 10% wt % of the composition; and
   wherein the composition attains a viscosity of less than about 2000 cps; and
   wherein the composition attains a concentration of solids from about 10 wt % to about 50 wt %; and
   wherein the average particle size of the polymer in the composition is less than about 20 microns; and
   wherein the composition is substantially free SLS; and
   wherein the composition is suitable for use in personal care compositions.

Typical water-insoluble polymers of the invention are the alkylcelluloses and the surfactants are non-SLS types including, but not limited to $C_{10}$-$C_{20}$ olefin sulfonates, phosphates and amphoteric surfactants and mixtures thereof.

In another aspect the invention provides a method for the production of an aqueous dispersion of an alkylcellulose polymer wherein the dispersion is substantially free of sodium lauryl sulfate comprising the steps of:

a) providing an alklycellulose;
b) providing at least one surfactant;
c) providing at least one stabilizer comprising a non-volatile alcohol having 12 or more carbons;
d) subjecting the reactants of parts a)-c) to the action of comminuting forces sufficient to produce an aqueous homogenous emulsion; and
e) recovering the aqueous homogenous emulsion of d) wherein said homogenous emulsion contains polymer having an average particle size of less than 20 microns.

In another embodiment the invention provides personal care products such as sunscreens which are substantially free of SLS and improved SPF functionality.

DETAILED DESCRIPTION OF THE INVENTION

Unless otherwise specified all references cited herein are incorporated by reference in their entirety.

The following definitions may be used for the interpretation of the claims and specification:

As used herein, the terms “comprises,” “comprising,” “includes,” “including,” “has,” “having,” “contains” or “containing,” or any other variation thereof, are intended to cover a non exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, “or” refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles “a” and “an” preceding an element or component of the invention are intended to be nonrestrictive regarding the number of instances (i.e. occurrences) of the element or component. Therefore “a” or “an” should be read to include one or at least one, and the singular word form of the element or component also includes the plural unless the number is obviously meant to be singular.

The term “invention” or “present invention” as used herein is a non-limiting term and is not intended to refer to any single embodiment of the particular invention but encompasses all possible embodiments as described in the specification and the claims.

As used herein, the term “about” modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term “about” also encompasses amounts that differ due to different equilibrium conditions for a composition resulting from a particular initial mixture. Whether or not modified by the term “about”, the claims include equivalents to the quantities. In one embodiment, the term “about” means within 10% of the reported numerical value, preferably within 5% of the reported numerical value.

The term Sodium lauryl sulfate shall be abbreviated as “SLS”.

The term “SPF agent” and “UV protectorant” will be used interchangeably and will refer to a compound that has the effect of blocking ultraviolet radiation or reflecting such radiation. Typical SPF agents will include but are not limited to titanium dioxide, zinc oxide, avobenzone, benzophenone 8, Octocrylene and oxybenzone.

The term “substantially free of SLS” or “having substantially no SLS” or substantially eliminating SLS” shall be used interchangeably and shall mean that the aqueous dispersion of a water insoluble polymer of the invention or a composition comprising the same which has less than 0.5 wt %, SLS.

The term "water insoluble polymer" means any water-insoluble polymer that is liquefiable at a temperature below the boiling point of contained volatile solvent used to dissolve the polymer.

The term "alternate surfactant" means any surface active agent that is suitable for the replacement of SLS in the compositions of the invention and are typified by nonionic or anionic oil-in-water functioning, ($C_{10}$-$C_{20}$) olefin sulfonates; phosphates; salts of C10-C20 glycinates and amphoteric surfactants and mixtures thereof.

The term "alkylcellulose" or "alkyl cellulose" will be used interchangeably and will refer to a water-insoluble polymer cellulose derivative where various hydroxyl groups of the repeating glucose units are substituted with alkyl or alkyl ether groups. Exemplary in the present invention is ethyl cellulose (CAS Number 9004-57-3), which is a preferred water insoluble polymer herein.

The term "personal care formulation" or "cosmetic formulation" will be used interchangeably and means a composition or formulation comprising ingredients particularly suited to treating, conditioning, hydrating or coloring the skin. Personal care formulations will typically contain for example diluent, thickeners, humectants, neutralizers, emulsifiers, solidifiers, occlusives, and colorants. The personal care formulations will additionally include those that are applied to the skin for therapeutic reasons and will have pharmaceutical efficacy.

The present application describes a composition suitable for use in personal care products, wherein the composition has substantially no sodium lauryl sulfate. The composition comprises a water-insoluble polymer in the form of an aqueous dispersion, where derivatives of cellulose polymers are preferred, and comprising an alternate surfactant or surface active agent which is not SLS.

Aqueous Dispersion of Water-Insoluble Polymers

An aqueous dispersion as described herein comprises a water-insoluble polymer dispersed in an aqueous medium. Any water-insoluble polymer that or is liquefiable at a temperature below the boiling point of the volatile organic solvent used to dissolve the polymer can be suitable for use in the practice of this invention. For example, a water insoluble polymer can be one selected from the group consisting of; homo- and copolymers of acetate, styrene polymers and copolymers, acrylic acid and acrylate ester polymers and copolymers, for example; nylons, polyalkyl ethers, and cellulose derivatives such as cellulose acetate and alkyl cellulose polymers. The listing of suitable water-insoluble polymers provided herein is not exhaustive. One of ordinary skill in the art would be able to select a suitable polymer based on the description provided herein. In one preferred embodiment, an aqueous dispersion as described herein comprises an alkylcellulose derivative, and more particularly the aqueous dispersion comprises ethylcellulose, as the water-insoluble polymer.

Alkylcellulose

The alkylcellulose of the invention is a cellulose alkyl ether comprising a chain formed from β-anhydroglucose units linked together via acetal bonds. Each anhydroglucose unit contains three replaceable hydroxyl groups, all or some of these hydroxyl groups being able to react according to the following reaction;

$RONa + C_2H_5Cl \rightarrow ROC_2H_5 + NaCl$, in which R represents a cellulose radical. Advantageously, the alkylcellulose is chosen from methylcellulose, ethylcellulose and propylcellulose. Preferred for use herein is ethylcellulose.

The ethylcellulose polymers used in a cosmetic composition according to the invention are preferentially polymers with a degree of substitution with ethoxy groups ranging from 2.5 to 2.6 per anhydroglucose unit, in other words comprising a content of ethoxy groups ranging from 44% to 50%.

According to a preferred mode, the ethylcellulose is used in a composition of the invention in the form of particles dispersed in an aqueous phase, like a latex or a pseudolatex type. The techniques for preparing these latex dispersions are well known to those skilled in the and discussed below.

The product sold by the company FMC Biopolymer under the name AQUACOAT™ ECD, which consists of a dispersion of ethylcellulose at a rate of 24.5%-29.5% by weight in water and stabilized with sodium lauryl sulfate and cetyl alcohol, is most particularly suitable for use as an aqueous dispersion of ethylcellulose.

According to one particular embodiment, the aqueous dispersion of ethylcellulose, in particular the product AQUACOAT™ ECD, may be used in a proportion of from 0.5% to 90% by weight, in particular from 1.0% to 60% by weight and preferably from 2%-40% by weight of ethylcellulose dispersion relative to the total weight of the cosmetic or personal care composition.

Preparation of Dispersions of Water-Insoluble Polymers

Alkylcellulose dispersions of the present invention can be prepared as described in U.S. Pat. No. 4,177,177, incorporated herein by reference as if fully set out, except that the present invention does not include the substantial use of sodium lauryl sulfate, and instead utilizes alternative surfactants.

The dispersions of the present invention can be obtained by: (1) obtaining a crude emulsion by emulsifying a liquefied water-insoluble polymer in an aqueous liquid medium containing at least one alternate nonionic or anionic oil-in-water functioning surfactant, all in the presence of at least one stabilizer comprising a non-volatile alcohol having 12 carbons or more or mixtures thereof; (2) subjecting the crude emulsion from step (1) to the action of comminuting forces sufficient to produce an aqueous homogenous emulsion (i.e., dispersion) containing polymer particles averaging less than about 100 microns or 90 microns or 80 microns or 70 microns or 60 microns or 50 microns or 40 microns or 30 microns or 20 microns or 10 microns or 1 micron or 0.5 microns where less than about 0.5 microns is preferred.

It can be important to maintain the temperature of the crude emulsion at a temperature that is sufficiently high (e.g., at least about 40° C.-85° C., or 45° C.-80° C. or 50° C.-75° C.) to lower the viscosity of the crude mixture prior to the homogenization step since high internal viscosity of the emulsion can prevent the particle size reduction. Extra heat maybe generated during the homogenization process. In that case, ice water can be used in the homogenizer to reduce the temperature to avoid temperatures that are considered to be too high. If the temperature becomes too high (e.g., over 100° C.), the polymer may become destabilized or can be burned or charred. Heating or cooling may alternately be required to maintain the temperature of the mixture and/or maintain the viscosity of the polymeric dispersion within operable limits, as well as preserve the stability of the polymer.

Typically an organic solvent will be used to liquefy a water-insoluble polymer that is not a liquid under the process conditions. In such cases the organic solvent can be removed after emulsion by appropriate methods. The water-insoluble polymer can be dissolved in an organic solvent prior to combining with the aqueous portion, typically in an amount such that the polymer is present in an amount of from about 5% to about 75%, or from about 10% to about 60%, or from about 15% to about 50% of the polymer mixture. The solvent is typically a volatile low molecular weight solvent.

Suitable volatile organic solvents include, for example: aromatic, aliphatic, or alicyclic hydrocarbons derivatives thereof, such as toluene, benzene, ethyl benzene, methyl isobutyl ketone, butyl methyl ketone, diethyl ether, sec-cutyl ether, petroleum ether, ligroin, propyl acetate, butyl acetate, iso-butyl acetate, amyl acetate, iso-amyl acetate, cyclohexene, pentane, hexane, heptane, cyclopentane, cyclohexane, hexane, for example. Other volatile solvents not listed herein can also be suitable, and the listing is not considered to be exhaustive. A mixture of any of these solvents is suitable for the practice herein.

Ethyl cellulose should comprise from about 5% to about 75%, or from about 10% to about 60%, or from about 15% to about 50% of the mixture, based on the total weight of the polymer/solvent mixture.

Optionally the composition of the invention may comprise a stabilizer in the form of a non-volatile alcohol having 12 carbons or more. The non-volatile alcohol is typically included in an amount of from about 0.2% to about 12%, or from about 0.4% to about 6% based on the weight of the polymer portion.

Final mixtures of the aqueous dispersion will generally attain a solids content from about 10 wt % to about 50 wt % of the polymer mixture where a content of about 20 wt % or 40 wt % is preferred and content of about 25 wt % to about 35 wt % is most preferred.

Alternate Surfactants

The composition of the invention may utilize an alternate surfactant. Suitable surfactants will generally be nonionic or anionic oil-in-water functioning surfactant and may include but are not limited to, ($C_{10}$-$C_{20}$) olefin sulfonates; phosphates, salts of C10-C20 glycinates amphoteric surfactants such as amino acids and amino acid derivatives, and particularly $C_{10}$-$C_{20}$ betaines such as lauryl betaine, or $C_{10}$-$C_{20}$ glutamate salts such as sodium lauroyl glutamate salts, sarcosine, and taurine (2-aminoethane sulfonic acid); as well as ether carboxylates such as polyoxyethylene alkylene ether carboxylates, or mixtures of any of these.

Whereas in many personal care compositions and products it is desirable to completely eliminate SLS in other compositions and products there may be a benefit to maintaining low levels of SLS. It will be appreciated by the skilled artisan that the compositions of the invention are equally well suited to partial replacement of SLS as they are to compositions having no such surfactants.

When choosing an alternate surfactant, amphoteric surfactants can be particularly useful. Amphoteric surfactants (zwitterionic surfactants) are surfactants that comprise both anionic and cationic functionality, and can alternatively have a net positive charge, a net negative charge, or no net charge depending on the pH of the medium in which they are used. The cationic functionality can be provided by an amino- or an ammonium group, while the anionic functionality can be provided by a carboxylate, sulfonate, or phosphate group, for example. Amphoteric surfactants have many benefits, particularly in cosmetic applications as described herein. It is generally known that amphoteric surfactants are dermatologically mild, have good detergency, are useful over a wide pH range, have excellent biodegradability, are compatible with other surfactant types, have anti-bacterial properties, reduce skin irritation, and provide good hydration and moisturizing capability. Amphoteric surfactants can be useful in some cosmetic applications where sodium lauryl sulfate is generally considered not to be useful or desirable. Use of amphoteric surfactants as described herein can thereby expand the use of alkylcellulose dispersions as described herein. Amphoteric surfactants described here include, for example: amino acids and amino acid derivatives, particularly betaines such as lauryl betaine, $C_{10}$-$C_{20}$ glutamate salts such as sodium lauroyl glutamate salts, sarcosine, and taurine (2-aminoethane sulfonic acid) alkyl iminopropionates; amido-betaines such as cocamido betaine, lauryl betaine, coco-betaine; amphoacetates such as cocoamphoacetate, and sodium cocoamphoacetate, for example.

Personal Care Products and Compositions

The aqueous dispersions described herein comprise substantially no SLS and surprisingly do not sacrifice functional or aesthetic properties required for use in certain personal care products. Some dispersions as described herein can surprisingly improve the functionality of cosmetic formulations, and facilitate the incorporation of such dispersions into new and different cosmetic or personal care formulations than those where SLS-containing dispersion are not generally used. For the purposes of the present invention, personal care products are products used, or intended to be used, for personal grooming and/or personal hygiene, or to improve the health and well being of an individual user.

Preferred in the present invention are personal care formulations and composition that have application for skin care as for example: skin moisturizers; perfumes; lip products such as lipsticks, lip stain, lip gloss; fingernail polishes and nail colors; eye and facial makeup preparations such as concealer and eye liner/pencil; some personal cleansers such as shampoos and body washes; hair products such as conditioners, permanent waves and hair colors; toothpastes; temporary tattoos; deodorants; skin protectants (such as lip balms and diaper ointments), lotions, sunscreens, antiperspirants, topical skin products, and treatments for dandruff or acne. This listing is only to present examples of personal care products, and not intended to limit the application or use of the present invention.

Some personal care products are intended for direct contact with the skin of a user. Some applications require skin contact for a short period of time, and the products are not intended for prolonged or continuous contact with the skin of a user. Such personal care products are typically intended to perform a function and then be removed from the skin by washing and/or thorough rinsing. Due to the transient nature of the contact with the skin, such products sometimes include higher percentages of SLS. For example, body washes, shampoos, conditioners are typically rinsed thoroughly after use and can generally comprise higher concentrations of SLS before encountering serious drawbacks. A prolonged period of time, as contemplated here, generally is at least about 30 minutes or more, for example; however it may be a shorter period of time depending on other factors such as, for example, concentration, other components, and location of use. Typically, cosmetic personal care products are intended to be rubbed, poured, sprinkled, or sprayed on, introduced into, or otherwise applied to the human body for cleansing, beautifying, promoting attractiveness, or altering the appearance.

Among other functions, cosmetic personal care products of the present invention are used to: brighten; illuminate; moisturize; provide resiliency and long-lasting effect; protect against the environment, weather and climate; provide a moisture barrier to keep moisture in and/or water out; provide a barrier to keep chemicals from penetrating the skin; protect active ingredients from being washed out. In part due to the manner in which cosmetic personal care products are used, it can be desirable to substantially eliminate SLS in such products and thereby reduce the potential for undesired effects from SLS.

Cosmetic personal care products have varying formulations depending on their use and applications. For example, a skin lotion will generally include both water soluble and oil soluble ingredients held together in an emulsification system (glycerol stearate and stearic acid). Optionally these formulations may include occlusive agents (petrolatum, mineral oil, dimethicone etc.) that create a barrier and block water loss. Optionally skin lotion formulations may include a humectant with attract water such as glycerin. Emollients (coconut oil, cetyl esters and silicones for example) may additionally be added to improve the feel of the lotion. A typical skin lotion formulation is given below:

| Purpose | Ingredient | Wt % |
|---|---|---|
| Diluent | Water | 79.6 |
| Thickener | Carboner | 5.0 |
| Humectant | Glycerin | 3.0 |
| Preservative | Methylparaben | 0.1 |
| Neutralizer | Triethanolomine | 0.9 |
| Coemulsifier | Cetyl Alcohol | 2.0 |
| Emulsifier | Stearic Acid | 0.8 |
| Emulsifier | Glyceryl Stearate SE | 1.5 |
| Preservative | Polybaraben | 0.05 |
| Occlusive | Isopropyl Myirstate | 1.5 |
| Occlusive | Mineral oil | 5.0 |
| Fragrance | Fragrance | 0.5 |

Another cosmetic formulation for use in the present invention are lipsticks, the primary ingredient in lipstick includes a solidifier (beeswax, Carnauba wax), diluent oils (jojoba esters, castor oil) and colorants (Red 7, red iron oxide). A typical lipstick formulation is given below:

| Purpose | Ingredient | Wt % |
|---|---|---|
| Diluent | Castor Oil | 6.2 |
| Solidifier | Octyl Palmitate | 10.0 |
| Solidifier | Carnauba wax | 4.0 |
| Solidifier | Ceresin | 10.0 |
| Solidifier | Microcrystalline was | 6.0 |
| Preservative | Methylparaben | 0.2 |
| Preservative | Propylparaben | 0.1 |
| Diluent | Cyclomethicone | 42.0 |
| Pigment dispersion | Dimethiconol beeswax | 1.0 |
| Colorant | Red 7 | 3.5 |
| Colorant | Red 6 | 0.5 |
| Colorant | Mic and methicone | 7.5 |
| Colorant | Bismuth oxycholoride | 6.0 |

Sunscreen formulations are another important application for the present invention. In addition to the underlying skin adaptive formulation elements, sunscreens will contain UV protectorant compounds/SPF agents that either block or reflect sunlight, or compounds that absorb sunlight and convert it to other forms of energy, e.g. heat. The most common actives in sunscreen formations include titanium dioxide, zinc oxide, avobenzone, benzophenone 8, Octocrylene and oxybenzone. In addition to the UV protectorant/SPF agent sunscreens will often contain occlusive agents and agents that block water loss as well as humectants and emollients as described above.

Replacement of SLS in Personal Care Products and Compositions

There are a number of beneficial effects associated with the replacement of or the substantial elimination of SLS as a surfactant in personal care products, the most prominent being a reduction in skin irradiation produced by SLS. By 'substantially eliminate SLS' it is meant that a dispersion as described herein includes less than 0.5 wt %, or less than 0.05 wt %, or less than 0.03 wt %, or less than 0.02 wt %, or less than 0.01 wt % of SLS, or alternatively the dispersion comprises 0 wt % SLS, that is, the aqueous dispersion includes no SLS.

Even small reductions in SLS concentrations may produce a noticeable reduction in skin irritation. In addition, applicants have unexpectedly discovered that reduction or elimination of SLS will decrease the incidence of the loss of effectiveness of actives in the products where an alkylcellulose polymer is part of the composition. For example it has been seen that replacement of SLS with the surfactants of the invention have the effect of both enhancing the effectiveness of SPF agents as well as preventing the loss of their effectiveness due to exposure or submersion in water. For example a sunscreen lotion of the invention comprising an alternate surfactant and an alkylcellulose polymer will provide greater water resistance and will require less SPF agent than a comparable lotion where the formulation does not contain an alkylcellulose dispersion. Accordingly, sunscreen lotions of the invention containing alternate surfactants and comprising ethylcellulose will commonly exhibit an ability to retain their SPF rating at least about 20%, or 25% or 30% or 35% or 40% or 45% or 50% or 55% or 60% or 65% or 70% or 75% longer when exposed to or submerged in water than a comparable sunscreen not comprising such a water insoluble polymer dispersion under the same conditions. Similarly, sunscreen lotions of the invention containing alternate surfactants and an alkylcellulose polymer will commonly exhibit an SPF boosting effect as compared with sunscreens not containing an alkylcellulose polymer dispersion. For example a sunscreen lotion containing alternate surfactants and ethylcellulose will require about 20% or 25% or 30% or 35% or 40% or 45% or 50% or 55% or 60%, or 65% or 70% or 80% less SPF agent than a comparable sunscreen lotion not containing an alklycellulose polymer dispersion.

In considering how to replace SLS various parameters should be considered. For example, one will need to consider electrolyte stability, elevated temperature stability, pH, viscosity, particle size and particle size distribution (PSD), because they are indicators of the long-term stability of the dispersion, and can be predictive of the flexibility and adaptability of the dispersions for use in a variety of formulations. Using these parameters applicants have determined that a dispersion of the present invention should have low viscosity. Low viscosity as the term is used herein is viscosity less than 2000 cps, or less than 1000 cps, or less than 500 cps, or less than 250 cps, or less than 150 cps, or less than 100 cps. Additionally, a dispersion of the present invention will comprise a surfactant or surfactant mixture in an amount of from about 0.1% to about 5%, based on the weight of the aqueous component of the dispersion.

PREFERRED EMBODIMENTS

In preferred embodiments of the invention the personal care formulations of the invention will comprise alternate surfactants as defined herein that will replace or substantially eliminate the presence of SLS. Many of these alternate surfactants are commercially available and go under the following non-limiting list of trade names, ETHOCEL™ 10NF, STEPANOL™ WA-100, BIO-TERGE™, AS-40, HOSTAPON™ KCG, EUMULGIN™ SG, MAPROSYL™ 30-B, MIRANOL™ HMA, AMPHOSOL™, AMPHOSOL™ CDB-HP 1C, MACKAM™ LB-35, GEROPON™ CG 3s, STEPAN™ SLL-FB, MACKADET™ 40-k and DERMALCARE™ MAP L-213/k. In addition to the aforementioned alternate surfactants the personal care formulations of the invention will additionally comprise ethylcellulose polymers in addition to those additives common in the industry for the preparation of personal care formulations.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

The following table 1 lists reagents and their sources used in the following examples.

TABLE 1

| Chemical Name | Source | Brand | Function |
|---|---|---|---|
| Cyclohexene | Alfa Aesar (Tewksbury, MA) | A11359 | Solvent |
| Cetyl alcohol (CA) | Peter Cremer (Cincinnati, OH) | CO-1695 | stabilizer |
| Ethylcellulose (EC) | DOW (Midland Michigan) | ETHOCEL ™ 10NF | Polymer |
| Sodium lauryl sulfate (SLS) | Stepan (Maywood NJ) | STEPANOL ™ WA-100 | Surfactant |
| Oleic acid | Spectrum Chemical Mfg. Corp (New Brunswick NJ) | Oleic acid NF | Surfactant |
| Sodium $C_{14-16}$ Olefin Sulfonate | Stepan (Maywood NJ) | BIO-TERGE ™ AS-40 | Surfactant |
| Sodium Stearyl Glutamate | BASF (Florham park NJ) | EUMULGIN ™ SG | Surfactant |
| Sodium lauroyl sarcosinate | Stepan (Maywood NJ) | MAPROSYL ™ 30-B | Surfactant |
| Sodium Lauroamphoacetate | Solvay (Princeton NJ) | MIRANOL ™ HMA | Surfactant |
| Coco betaine | Making Cosmetics (Redmond WA) | Coco betaine | Surfactant |
| Sodium Cocoyl Glycinate | Solvay (Princeton NJ) | GEROPON ™ CG 3s | Surfactant |

The following abbreviations are used in the examples:

"ECD" means ethyl cellulose dispersion.

"ECD-30" means ethyl cellulose dispersion with 30% solid content.

Unless otherwise specified the material used to make cosmetics formulations, were purchased from MakeCosmetics.com website (Redmond WA). AVICEL™ PC-591 was obtained directly from DuPont Nutrition and Health (Wilmington DE), while the ESP A+ Gel was kindly sampled from Earth Supplied Products, LLC.

Unless otherwise specified, all reagents, and materials used herein were obtained from Aldrich Chemicals (Milwaukee, WI), or Sigma Chemical Company (St. Louis, MO).

Electrolyte stability was tested with the following method: 10 g of ECD is mixed with 10 g 20% CaCl2 solution thoroughly using a glass rod. The mixture was then allowed to stand room temperature for 1 hour. The sample was then observed for changes, such as clots, coagulation or significant thickening. No changes indicate good stability.

Elevated temperature stability was tested with the following method: 25-30 g of ECD was placed in 50 mL vented plastic bottle and put in oven at 80° C. for 24 hours. The sample was then taken out and observed for changes.

In the Freeze/Thaw (F/T) stability test, 15 mL ECD-30 was added into 50 mL plastic centrifuge tube and put into freezer (−20° C.) for 24 hours. The frozen product was then taken out and let it thaw for 24 hours. Visual observation on the product was performed. Any changes such as viscosity increase, gelation, color change etc. were recorded. This is the first cycle. The procedure is repeated for 3 cycles.

The viscosity was measured with Brookfield RV viscometer at room condition (~70° F.), UL adapter at 30 rpm. The number was taken 1 minute after the spindle was turning in product.

The pH of the ECD was measured with a calibrated pH meter at room conditions (temperature ~70° F.).

The particle size and particle size distribution were taken with Malvern MASTERSIZER™-3000 particle analyzer with DI water as a medium, refractive index of 1.520 and absorption index of 0.010. Add about ¼ to ½ pipette of dispersion into a 600 ml beaker containing about 500 mL of media to achieve obscuration of 2-6%. Set stir speed of 1800 rpm and ultrasonicate at 100% for 5 seconds. Set pre-measurement delay of 120 seconds and took 3 measurements with 0 second delay.

Stickiness was tested with finger touching the film and qualitatively rated.

Sun screen samples were tested by IMS Inc (Portland ME) using their in-vitro Water Resistance Protocol. The test took measurements both prior to and after the samples have been immersed in a controlled temperature water bath 40° C. agitated at 300 rpm for 80 minutes. These conditions were slightly more aggressive than typical in vivo water resistance test conditions.

Example 1-1

Ethylcellulose Dispersion with Sodium ($C_{14}$-$C_{16}$) Olefin Sulfonate (for Example, BIO-TERGE™ AS-40 from Stepan)

An organic phase was prepared as follows: cetyl alcohol (13 grams) was combined with cyclohexene (403 grams) in a jacketed double walled 4-neck reactor connected to a water bath. The solution was agitated at room temperature until cetyl alcohol was fully dissolved in the cyclohexene. The water bath was then turned on and the temperature was set to 65° C. Ethylcellulose (136 grams) was added slowly into the reactor. The mixture was stirred at 65° C. for approximately 2 hours until the ethylcellulose was completely dissolved.

An aqueous phase was prepared as follows: de-ionized water (493 grams) was combined with sodium ($C_{14}$-$C_{16}$) olefin sulfonate (BIO-TERGE™ AS-40) (607 grams) in a jacketed double walled 3-neck round bottom flask under mild agitation at room temperature until the sodium ($C_{14}$-$C_{16}$) olefin sulfonate was dissolved, which took about 5-10 minutes.

A crude emulsion was made by keeping the organic phase and aqueous phase at 65° C. The organic phase was slowly transferred into the aqueous phase via a mechanical pump (Masterflex Digital Economy Drive L/S (#7524-40) equipped with a MASTERFLEX™ L/S Easy-Load II Pump Head (#77200-62)), through heated MASTERFLEX™ #36 Viton tubing. Agitation was maintained during the transfer, and for an additional 30 minutes after the transfer was completed. The crude emulsion had a milky white appearance.

The crude emulsion was taken from the water bath at 65° C. and homogenized with a Microfluidics #110Y equipped with a 75 micron interaction chamber. The crude emulsion was passed through the homogenizer for 3 passes at 9,000 psi.

The homogenized product was distilled via rotary evaporation on a water bath at 45° C. to remove volatiles, until a solids level of from about 30 wt % was obtained. The dispersion was filtered through a 75 micron screen and then packed into a plastic container for analysis. The resulted ECD had viscosity of 5 cps, pH 7 and average particle size of 0.4 micron.

Comparative Example 1-2

Ethylcellulose dispersion using SLS as surfactant was made the same method described in example 1. The dispersion is milky white, with low viscosity.

Example 1-3

Ethylcellulose dispersion using Coca Betaine (for example Coco Betaine from Making cosmetics LLC) as surfactant was made the same method described in example 1. The dispersion is milky white with viscosity of 8 cps and pH 7.8. The latex dispersion had an average particle size of 0.4 micron with tails. It passed the elevated temperature (80° C.) overnight without change and stayed stable in $CaCl_2$ salt solution.

Example 1-4

Sulfur-Free Ethylcellulose Dispersion with Sodium Oleate

Sodium hydroxide neutralized oleic acid was used as surfactant for a 100% replacement of SLS according to the process of the Example 1. A stable latex was obtained.

Example 1-5

Ethylcellulose dispersion using Sodium cocoamphoacetate (for example, MIRANOL™ HMA from Solvay) as surfactant was made the same method described in example 1. The dispersion is milky white with viscosity of 8 cps and pH 7.8. The latex dispersion had an average particle size of 0.4 micron with tails. It passed the elevated temperature (80° C.) overnight without change and stayed stable in $CaCl_2$ salt solution.

Example 1-6

Ethylcellulose dispersion using Sodium Cocoyl Glycinate (for example, GEROPON™ CG 3S from Solvay) as surfactant was made the same method described in example 1. The dispersion is milky white with viscosity of 31 cps and pH 7.4. The latex dispersion had an average particle size of 0.4 micron with a larger molecular weight tail. It passed the elevated temperature (80° C.) overnight without change and stayed stable in $CaCl_2$ salt solution except some soft clots were found on the sieve after went through the sieve.

Example 1-7

Ethylcellulose dispersion using Sodium lauroyl sarcosinate (for example, MAPROSYL™ 30-B from Stepan) as surfactant was made the same method described in example 1. The dispersion is milky white with viscosity of 10 cps and pH 7.2. The latex dispersion had an average particle size of 0.3 micron with a tail. It passed the elevated temperature (80° C.) overnight without change.

Example 1-8

Ethylcellulose dispersion using sodium stearoyl glutamate (for example, EUMULGIN™ SG from BASF) as surfactant was made the same method described in example 1. The dispersion is milky white with viscosity of 9 cps and pH 7.5. The latex dispersion had an average particle size of 0.3 micron with a tail. It passed the freeze/thaw stability and the elevated temperature stability tests without change. However, it thickened with soft clots with CaCl2 stability test.

The physical properties of the ECDs made in Examples 1-1 to 1-8 are summarized in Table 3 below.

TABLE 1

Physical properties of ECD made with selected SLS free surfactants

| Surfactant/ Example# | % Solids | pH | Visc, cps | PSD, $D_{50}$ | Stability 80C* | Stability $CaCl_2$* | Stability F/T |
|---|---|---|---|---|---|---|---|
| SLS/1-2 | 29.7 | 6.3 | 16 | 0.3 single | E | S | G |
| EUMULGIN ™ SG/1-8 | 28.7 | 7.5 | 9 | 0.3 1 tail | E | T, S | G |
| COCA BETAINE/ 1-3 | 28.9 | 7.8 | 8 | 0.4 2 tails | E | E | G |
| MAPROSYL ™ 30-B/1-7 | 28.9 | 7.2 | 10 | 0.3 1 tail | E | | E |
| GEROPON ™ CG 3S/1-6 | 29.9 | 7.4 | 31 | 0.4 Double peak | E | S | T |
| BIO-TERGE ™ AS40/1-1 | 26.1 | 7.1 | 5 | 0.4 single | E | S | E |
| NA OLEIC ACID/ 1-4 | 30.4 | 9.5 | 57 | 0.4 2 tails | C | T | N/A |

*S - Soft clots; T - Thickened; E - No changes; G - gelled; C - color changed to light brown; N/A - no data Example 2-1

A thick, viscous off-white cream base (obtained from Making cosmetics, Inc.) was obtained as a base to make moisturizing lotion. The cream base had the composition in Table 2.

TABLE 2

| Composition of Cream Base | |
|---|---|
| Ingredients | % weight |
| Aloe barbadensis (Aloe) Juice | 15-50% |
| Prunus dulcis (Sweet Almond) Oil | 15-50% |
| Emulsifying Wax | 4-15% |
| Stearic Acid | 4-15% |
| Glycerin | 4-15% |
| Tocopherol | 1-8% |
| Persea Americana (Avocado) Oil | 1-8% |
| Simmondsia Chinensis (Jojoba) Oil | 1-8% |
| Sheabutter | 1-8% |
| Xanthan Gum | 0.5-7% |
| Lecithin | 0.5-7% |
| Salix Alba (White Willow Bark) Extract | 0.5-7% |
| Azadirachta indica (Neem) Oil | 0.5-7% |
| Carbomer | 0.5-7% |
| Triethanolamone (TEA) | 0.5-3% |
| Rosmarinus Officinalis (Rosemary) Oleoresin | 0.5-3% |
| Tetrasodium EDTA | 0.5-3% |
| Citric Acid | 0.5-3% |
| Phenoxyethanol | 0.1-1% |

The cream base (A) was combined with the SLS solution in the following proportion: 77% by wt cream base A and 23% by wt of a 1.3% sodium lauryl sulfate (SLS) solution in DI water. The cream base was added into the SLS solution slowly under agitation (mild stirring). The mixture was mixed for additional 5 to 10 minutes after the addition is and the mixture became homogeneous. Formula 1 was a homogeneous white lotion and demonstrated good wear.

Comparative Example 2-2

Formula 2 lotion was made by substituting the 1.3% SLS solution to the ECD made in example 1-2 with the same procedures described in example 2-1. Formula 2 gave a non-homogeneous white lotion which had gritty particles suspended in the lotion.

Example 2-3

Formula 2-3 was made by substituting the 1.3% SLS solution to the ECD made in example 1-8 with the same procedures described in example 2-1. It is a homogeneous cream with higher viscosity than Formula 1 lotion in Examples 2-1. Skin hydration was measured over a 6-hour period and the composition exhibited improved hydration over time as compared to the lotion Formula 1 made in Example 2-1.

Example 3-1

A lip gloss was formulated using the formulation below.

Jojoba oil was added into ECD from example 1-2 slowly with mild agitation. The mixture was then heated to 55° C. and kept at that temperature for 1 hr. The surfactant mixture (see below) and polyvinyl alcohol were added one by one, each agitated to obtain a homogeneous mixture. The mixture was allowed to cool to room temperature. The ingredients listed in the table 3 below were added in the given amounts with stirring. A milky viscous lip gloss was obtained.

TABLE 3

| Lip Gloss formulation | |
|---|---|
| Ingredients | Weight, gram |
| ECD | 100.1 |
| Jojoba oil | 100.1 |
| Surfactant mixture (sorbitan stearate & sucrose cocoate) | 11.85 |
| Partially hydrated (88%) Polyvinyl alcohol | 1.5 |
| Polyphenyltrimethylsiloxy dimethylsiloxane | 69.0 |
| DI water | 6.5 |
| Non-denatured 96-degree ethanol | 9.0 |
| Phenoxyethanol | 1.5 |

The formulation had good wear, good shine and silky feel. It was slightly tacky.

Example 3-2

A lip gloss was formulated with ECD made in example 1-8 with the same procedures and use level in example 3-1. The lip gloss obtained was homogeneous, creamy and viscous. It was not tacky, comfortable to wear, and exhibited good hydration and good skin feel.

Example 4-1

The sunscreen lotions were prepared according to the formulation in the following table 4. During the preparation, AVICEL™ PC 591 was activated into DI water first by weighing Phase A water and glycerin and added into a Waring Blender cup (any high shear mixer can be used to substitute the Waring Blender). Slowly bring the blender speed up to form a vortex and then add AVICEL™ PC 591 slowly to the center of the water. Increase the speed to maximum when the AVICEL™ addition is completed and keep blending for 1 minute.

The AVICEL™ dispersion was then transferred into a beaker with lightening mixer. Zinc oxide and ECD from example 1-2 were added under moderate mixing until a uniform suspension is obtained. Gently heat mix to ~70° C.

Combine all phase B ingredients in a secondary beaker heat under moderate mixing to 75-80° C. Slowly add B to A. Maintain gentle mixing until cooling to <35° C. and add A+ Gel, preservative and fragrance. Mix moderately until fully dispersed. Continue to cool to <30° C. with agitation and package.

TABLE 4

| Sunscreen lotion formulations | | |
|---|---|---|
| Ingredient | Function | Use Level |
| Phase A | | |
| DI Water | Solvent | 62.40 |
| Avicel PC 591 | Rheology Modifier | 1.25 |
| Glycerin | Emollient | 2.00 |
| Zinc Oxide | UV Blocker | 5.00 |
| ECD | Film former | 4.00 |
| Phase B | | |
| Avobenzone | UV Filter | 3.00 |
| Octocrylene | UV Filter | 10.00 |
| Sorbitan Monooleate | Emulsifier | 5.00 |
| Cetyl alcohol | Thickener | 2.00 |

TABLE 4-continued

| Sunscreen lotion formulations | | |
|---|---|---|
| Ingredient | Function | Use Level |
| Phase C | | |
| ESP A+ Gel | Tactile control/Emollient | 5.00 |
| Paraben-DU | Preservative | 0.35 |
| | | 100.00 |

The formulations resulted a lotion with non sticky and clean feel. The in-vitro static SPF was 56, and became SPF 5 after 80 minutes in agitating at 300 rpm in water at 40° C.

Example 4-2

Same sunscreen lotion was made using the sample formula and procedure in example 4-1 but using DI water to replace the ECD. The lotion was non sticky and feels clean. The in-vitro static SPF was 50, and became SPF 6 after 80 minutes in agitating at 300 rpm in water at 40° C.

Example 4-3

Same sunscreen lotion was made using the sample formula and procedure in example 4-1 but used ECD made in example 1-8. The lotion was non sticky and feels clean. The in-vitro static SPF was 72, and became SPF 24 after 80 minutes in agitating at 300 rpm in water at 40° C.

Example 4-3

Same sunscreen lotion was made using the sample formula and procedure in example 4-1 but used ECD made in example 1-6. The lotion was non sticky and feels clean. The in-vitro static SPF was 64, and became SPF 15 after 80 minutes in agitating at 300 rpm in water at 40° C.

Example 4-4

Same sunscreen lotion was made using the sample formula and procedure in example 4-1 but used ECD made in example 1-7. The lotion was non sticky and feels clean. The in-vitro static SPF was 67, and became SPF 25 after 80 minutes in agitating at 300 rpm in water at 40° C.

The results from examples 4-1 to 4-5 are summarized in table 5 below.

TABLE 5

Effect of ECDs in model sunscreen formulations

| Example # | Surfactants used in the example ECD | % ECD in the formulation | Static SPF | SPF after 80 min in water |
|---|---|---|---|---|
| N/A | N/A | 0 | 50.1 | 5.5 |
| 1-2 | SLS | 4 | 55.7 | 5.4 |
| 1-8 | EMULGIN ™ SG | 4 | 72.1 | 23.7 |
| 1-6 | GEROPON ™ CG 3S | 4 | 64.0 | 15.1 |
| 1-7 | MAYPROSYL ™ 30-B | 4 | 66.8 | 24.7 |

Example 5

The skin care lotion was prepared according to the formulation in the following table 6.

The procedures to make the lotion is as following: In a support vessel heat Octyldodecanol to 85° C. with moderate propeller agitation (Phase A). Combine ingredients of Phase B. Slowly add into Phase A while mixing at 85° C. Agitate until completely uniform (Phase A/B). In a separate container mix the ingredients of Phase C at 85° C. until uniform (Phase C). Add Phase C to Phase A/B. Mix until completely uniform. Remove heat. Add ingredients in Phase D. Mix thoroughly.

TABLE 6

| Skin care lotion formulation | |
|---|---|
| Ingredient | Mayprosyl 30-B, % |
| Phase A | |
| Octyldodecanol | 20.00 |
| Phase B | |
| Cetearyl Alcohol | 2.00 |
| Cetyl alcohol | |
| Caprylic/Capric triglyceride | 10.00 |
| Phase C | |
| Deionized water | 54.65 |
| Glycerin | 3.00 |
| SLS | 0.05 |
| Cetyl alcohol | 0.10 |
| ECD | 3.85 |
| Phase D | |
| Deionized water | 5.00 |
| Magnesium sulfate | 0.70 |
| NiPaguard | 0.80 |
| Total | 100.00 |

The skin care lotion made from this formulation with ECD made in example 8 was easy to spread, no tacky and had a smooth and clean feel.

Example 6—Foundation

The ECD made in example 1-8 was also tested in a modified smooth foundation formulation, published in book (Karin Bombeli and T Bombeli, "Recipes for Makeup & Blush", MakingCosmetics Inc, 2$^{nd}$ edition, page 23 (2015)) and provided in Table 7 below. ECD was used to partially replace the water added into the formulation.

Mix Phase A into a glass beaker at room temperature. Add Phase B into a mortar and blend well with the pestle until the color is uniform. Then add Phase B to Phase A and stir. Sprinkle Phase C into phase A/B while stirring. Mix Phase D together in a separate beaker. Heat both beaker to 160° F./71° C. to melt the ingredients.

Add Phase D to Phase A/B/C and stir well until uniform. Then add ECD-30 into the mixture and stir in mild agitation to uniform. Remove from heat, continue stirring and cooling to 100° F./40° C. Finally, add Phase E and mix well.

TABLE 7

| Smooth Foundation formulation | | |
|---|---|---|
| Ingredient | Functions | Weight, g |
| Phase A | | |
| Distilled water | Diluent | 142.2 |
| Glycerin | Humectant | 6.0 |

TABLE 7-continued

| Smooth Foundation formulation | | |
|---|---|---|
| Ingredient | Functions | Weight, g |
| Polysorbate 80 | Emulsifier | 0.9 |
| Triethanolamine | Stabilizer | 1.8 |
| Phase B | | |
| Titanium Dioxide | Sunscreen | 15.0 |
| Pigment Blend Bare Neutral | Colorant | 13.5 |
| Mica spheres | Texturizer | 24.0 |
| Phase C | | |
| Hyaluronic Acid | Moisturizer | 0.6 |
| Xanthan Gum | Thickener | 1.5 |
| Phase D | | |
| Triglyceride | Emollient | 31.5 |
| OM-Cinnamate | UV-Filter | 15.0 |
| Stearic Acid | Emulsifier | 7.5 |
| CreamMaker Blend | Emulsifier | 4.5 |
| Cetyl Alcohol | Thickener | 4.5 |
| Vitamin E Acetate | Vitamin | 1.5 |
| ECD | Film former | 18.0 |
| Phase E | | |
| Paraben-DU | Preservative | 3.0 |
| TOTAL | | 291.0 |

The resulted foundation was smooth and stable. It was easy to spread, had a nice clean and light feeling. It was non-sticky on skin.

What is claimed is:

1. An aqueous dispersion composition comprising:

a) ethylcellulose;

b) coco betaine; and c) a stabilizer comprising a non-volatile alcohol having 12 carbons or more;

wherein the coco betaine comprises from about 0.1 wt % to about 10 wt % of the composition; and wherein the aqueous dispersion composition has a viscosity of less than about 2000 cps; and wherein the aqueous dispersion composition has a concentration of solids from about 20 wt % to about 50 wt %; and wherein the average particle size of the ethylcellulose in the aqueous dispersion composition is less than about 20 microns; and wherein the aqueous dispersion composition is substantially free of sodium lauryl sulfate (SLS); and wherein the aqueous dispersion composition is suitable for use in personal care compositions.

2. A method for the production of an aqueous dispersion of ethylcellulose wherein the dispersion is substantially free of sodium lauryl sulfate comprising the steps of:

a) providing the ethylcellulose;

b) providing coco betaine, wherein the coco betaine comprises from about 0.1 wt % to about 10 wt % of the aqueous dispersion;

c) providing at least one stabilizer comprising a non-volatile alcohol having 12 or more carbons;

d) subjecting the reactants of parts a)-c) to the action of comminuting forces sufficient to produce an aqueous homogenous emulsion; and e) recovering the aqueous homogenous emulsion of d) wherein the aqueous homogenous emulsion contains ethylcellulose having an average particle size of less than 20 microns, wherein the aqueous homogenous emulsion has a concentration of solids from about 20 wt % to about 50 wt %, wherein the aqueous homogenous emulsion has a viscosity of less than about 2000 cps, and wherein the aqueous homogenous emulsion is suitable for use in personal care compositions.

3. The method of claim 2 wherein the ethylcellulose polymer is dissolved in an organic solvent.

4. A personal care product comprising the composition of claim 1 wherein the personal care product is selected from the group consisting of cosmetics, fingernail polishes, nail colors, facial makeup preparations, shampoos, body washes, hair conditioners, permanent waves, hair colors, toothpastes, temporary tattoos, deodorants, skin protectants, skin moisturizers, lotions, sunscreens, antiperspirants, perfumes, topical skin products, and treatments for dandruff or acne.

5. A sunscreen lotion comprising the composition of claim 1.

6. A sunscreen lotion comprising the composition of claim 1 and having a reduced amount of SPF agent as compared with a comparable lotion which lacks the aqueous dispersion and wherein the lotions have equivalent SPF ratings.

7. The aqueous dispersion composition of claim 1, wherein the concentration of solids is between about 20 wt % to about 40 wt %.

8. The aqueous dispersion composition of claim 1 wherein the concentration of solids is between about 25 wt % to about 35 wt %.

9. The aqueous dispersion composition of claim 1 wherein the viscosity is less than 500 cps.

10. The aqueous dispersion composition of claim 1 wherein the viscosity is less than 250 cps.

11. The aqueous dispersion composition of claim 1 wherein the viscosity is less than 100 cps.

12. The sunscreen lotion of claim 6, wherein the SPF agent is selected from the group consisting of titanium dioxide, zinc oxide, avobenzone, benzophenone 8, octocrylene, and oxybenzone.

13. A smooth foundation formulation comprising the aqueous dispersion composition of claim 1.

* * * * *